US009433374B2

(12) United States Patent
Goto et al.

(10) Patent No.: US 9,433,374 B2
(45) Date of Patent: Sep. 6, 2016

(54) CONCENTRATION MEASURING DEVICE AND A METHOD OF CONTROLLING THE CONCENTRATION MEASURING DEVICE

(71) Applicant: SEIKO EPSON CORPORATION, Tokyo (JP)

(72) Inventors: Kenji Goto, Aichi (JP); Hideaki Yamada, Shimosuwa-machi (JP); Kazuhiro Nishida, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 13/957,800

(22) Filed: Aug. 2, 2013

(65) Prior Publication Data

US 2014/0039282 A1    Feb. 6, 2014

(30) Foreign Application Priority Data

Aug. 6, 2012    (JP) ................. 2012-174097

(51) Int. Cl.
  *A61B 5/1455*    (2006.01)
  *A61B 5/145*     (2006.01)
  *A61B 5/00*      (2006.01)

(52) U.S. Cl.
  CPC ......... *A61B 5/14552* (2013.01); *A61B 5/0059* (2013.01); *A61B 5/14532* (2013.01)

(58) Field of Classification Search
  CPC .................................................. A61B 5/1455
  USPC ................................................ 600/310–344
  See application file for complete search history.

(56) References Cited

U.S. PATENT DOCUMENTS

| 5,168,326 A | * | 12/1992 | Tokieda et al. ............... 356/368 |
| 5,535,743 A | * | 7/1996 | Backhaus et al. ............ 600/310 |
| 6,166,807 A | | 12/2000 | Kawamura et al. |
| 6,466,320 B1 | | 10/2002 | Kawamura et al. |
| 2010/0004518 A1 | * | 1/2010 | Vo ....................... A61B 5/14532 600/310 |
| 2013/0033707 A1 | | 2/2013 | Yamada et al. |

FOREIGN PATENT DOCUMENTS

| JP | 09-138231 A | 5/1997 |
| JP | 2004-081284 A | 3/2004 |
| JP | 2004-113434 A | 4/2004 |
| JP | 2013-036792 A | 2/2013 |

OTHER PUBLICATIONS

Wood et al.; "Multivariate analysis methods for spectroscopic blood analysis"; Proc. of SPIE, vol. 8219, 821909-1-821909-9.

* cited by examiner

*Primary Examiner* — Tse Chen
*Assistant Examiner* — Marjan Fardanesh
(74) *Attorney, Agent, or Firm* — Global IP Counselors, LLP

(57) ABSTRACT

In a concentration measuring device, a measuring light in a wavelength region where an absorbance related to the water in a subject can be practically ignored is irradiated to the subject by a light source. The transmitted light transmitted through the subject is received in a light receiving part. An optical rotation calculation part calculates an optical rotation of the subject by using an output signal from the light receiving part, and an absorbance calculation part calculates an absorbance of the subject by using an output signal from the light receiving part. A concentration calculation part calculates a concentration of glucose by using a glucose measurement data related to an aqueous solution of simple glucose, a protein measurement data related to an aqueous solution of simple protein, the optical rotation calculated by the optical rotation calculation part, and the absorbance calculated by the absorbance calculation part.

10 Claims, 7 Drawing Sheets

CONCENTRATION MEASURING DEVICE AND A METHOD OF CONTROLLING THE CONCENTRATION MEASURING DEVICE

CROSS-REFERENCE TO THE RELATED APPLICATION

This application claims priority to Japanese Patent Application No. 2012-174097 filed on Aug. 6, 2012. The entire disclosure of Japanese Patent Application No. 2012-174097 is hereby incorporated herein by reference.

TECHNOLOGICAL FIELD

The present invention relates to a concentration measuring device, and the like to measure a concentration of a selected component in a subject.

BACKGROUND TECHNOLOGY

A method for analyzing a component of a substance by measuring light that was transmitted through the substance is known. For example, when a polarized light directly passes through an optically active substance such as glucose, a phenomenon so-called an optical rotation that the plane of polarized light rotates is known. Also, a technology that a concentration is measured by using a phenomenon so-called absorbent that absorbs light, which was transmitted through the substance and is changed in accordance with a type or a concentration of substances, is proposed (e.g., Patent Documents 1 and 2).

PRIOR ART DOCUMENT

Patent Document

[Patent Document 1] Japanese Laid-open Patent Application No. 2004-81284
[Patent Document 2] Japanese Laid-open Patent Application No. 2004-113434

DISCLOSURE OF THE INVENTION

Problems to be Solved by the Invention

When a measurement is performed to a subject as a target and the subject includes water, the existence of the water became a problem in the conventional concentration measurement method. For example, it is known to use the vicinity of infrared light as measuring light. However, in the wavelength region of the vicinity of infrared light, many peaks of absorption of water are existed. Specifically, the presence of the water gets in the way in the concentration measurement which uses the adsorption. That is, the absorbance of a component as a measuring subject is absorbed in the absorbance of water so that there was a problem that the component of the measuring subject and the water cannot be separated. In addition, the absorbance of water is easily affected by the temperature fluctuation, and even though the temperature changes slightly, the absorbance changes dramatically.

For example, when the measurement of a blood-sugar level for an organism as a subject is performed, it may consider the configuration that a measurement is performed by applying measuring light to a peripheral portion such as a fingertip or an earlobe. However, in the normal measurement environment, the temperature fluctuation occurs due to the outside air temperature so that by having a great effect on the absorption of water as described above and its temperature dependability, there was a problem that an improvement of the measurement accuracy cannot be expected.

The present invention is made in consideration of the above described problems, and an object of the present invention is to propose a new method for measuring a proper concentration of a selected component of a subject including water.

Means Used to Solve the Above-Mentioned Problems

According to the first embodiment in order to resolve the above problems, a concentration measuring device measures a concentration of a first component of a subject. The subject includes water, and also includes the first component and a second component having an optical rotation and an absorbent. The concentration measuring device is provided with an irradiation part irradiating measuring light to the subject in a wavelength region where an absorbance related to the water in the subject can be practically ignored; a light receiving part receiving transmitted light, which was transmitted through the subject; an optical rotation calculation part calculating an optical rotation of the subject by using an output signal from the light receiving part; an absorbance calculation part calculating an absorbance of the subject by using the output signal from the light receiving part; a concentration calculation part calculating the concentration of the first component by using a first measurement data related to an aqueous solution of the simple first component, a second measurement data related to an aqueous solution of the simple second component, the optical rotation calculated by the optical rotation calculation part, and the absorbance calculated by the absorbance calculation part.

According to another embodiment, a method for controlling a concentration measuring device to measure a component concentration of a subject, wherein the concentration measuring device is provided with an irradiation part irradiating measuring light to the subject and a light receiving part receiving light transmitted through the subject, the controlling method including the steps of: irradiating the measuring light in a wavelength region where an absorbance of water in the subject can be practically ignored and wherein the subject includes water, and a first component and a second component that have an optical rotation and an absorbent; calculating an optical rotation of the subject by using an output signal from the light receiving part; calculating an absorbance of the subject by using an output signal from the light receiving part; and calculating a concentration of the first component by using a first measurement data related to an aqueous solution of the simple first component, a second measurement data related to an aqueous solution of the simple second component, the optical rotation calculated by the optical rotation calculation part, and the absorbance calculated by the absorbance calculation part.

According to the first embodiment, and the like, the measuring light in the wavelength region where the absorbance of water in the subject can be practically ignored is irradiated to the subject. The transmitted light that transmits through the subject is received in the light receiving part. The optical rotation calculation part calculates the optical rotation of the subject by using an output signal from the light receiving part, and the absorbance calculation part calculates the absorbance of the subject by using an output signal from the light receiving part. Then, the concentration calculation part calculates the concentration of the first component by using a first measurement data related to an aqueous solution of the simple first component, a second measurement data related to an aqueous solution of the simple second component, the optical rotation calculated by the optical rotation calculation part, and the absorbance calculated by the absorbance calculation part. By performing a measurement by using the measuring light in the wavelength region where the absorbance of water in the subject can be practically ignored, it becomes possible to measure a proper concentration of a selected component in a subject without the effect of the absorption of water.

Also, as the second embodiment, in the concentration measuring device of the first embodiment, the concentration measuring device may have the following configuration. The subject is an organism. The first component is glucose. The second component is protein. The irradiation part defines the wavelength region that is 400 nm to the vicinity of 1300 nm.

According to the second embodiment, the subject is an organism. The first component is glucose, and the second component is protein. Also, the irradiation part is in the wavelength region of 400 nm to the vicinity of 1300 nm. In this wavelength region, it becomes possible to measure the concentration of glucose in the subject as the organism without the effect of the absorption of water.

In this case, as the third embodiment, in the concentration measuring device of the second embodiment, the concentration measuring device may have the following configuration. The irradiation part irradiates the measuring light for optical rotation in the wavelength region of 400 nm to 800 nm. The optical rotation calculation part calculates an optical rotation by using an output signal from the light receiving part when the measuring light for optical rotation was irradiated.

According to the third embodiment, the wavelength region 400 nm to 800 nm is used for the calculation of the optical rotation so that in the measurement of the second embodiment, it becomes possible to calculate the optical rotation with good accuracy.

Further, as the fourth embodiment, in the concentration measuring device of the second embodiment or the third embodiment, the concentration measurement device may have the following configuration. The irradiation part irradiates the measuring light for absorbance in any of the wavelength regions of 400 nm to 900 nm, the vicinity of 1100 nm, the vicinity of 1190 nm and the vicinity of 1300 nm. The absorbance calculation part calculates an absorbance by using an output signal from the light receiving part when the measuring light for absorbance was irradiated.

According to the fourth embodiment, the wavelength regions of any of 400 nm to 900 nm, the vicinity of 1100 nm, the vicinity of 1190 nm, and the vicinity of 1300 nm are used for the calculation of the absorbance so that in the measurement of the second embodiment or the third embodiment, it becomes possible to calculate the absorbance with good accuracy.

Also, as the fifth embodiment, in the concentration measuring device of any of the first embodiment to the fourth embodiment, the concentration measuring device has the following configuration. The irradiation part irradiates the measuring light by changing a wavelength in the wavelength range. The optical rotation calculation part calculates optical rotations corresponding to a plurality of wavelengths. The absorbance calculation part calculates absorbance corresponding to the plurality of wavelengths. The concentration calculation calculates a concentration of the respective first component and second component by performing a predetermined multivariate analysis by using the plurality of optical rotations calculated by the optical rotation calculation part and the plurality of absorbance calculated by the absorbance calculation part in reference to the first measurement data and the second measurement data.

According to the fifth embodiment, the irradiation part irradiates the measuring light by changing a wavelength in the wavelength range. The optical rotation calculation part calculates optical rotations corresponding to a plurality of wavelengths, and the absorbance calculation part calculates absorbance corresponding to the plurality of wavelengths. Then, the concentration calculation calculates a concentration of the respective first component and second component by performing a predetermined multivariate analysis by using the plurality of optical rotations calculated by the optical rotation calculation part and the plurality of absorbance calculated by the absorbance calculation part in reference to the first measurement data and the second measurement data. The optical rotations and the absorbance corresponding to the plurality of wavelengths are calculated, and the predetermined multivariate analysis is performed by using these values so that it becomes possible to calculate the concentrations of the first component and the second component with high accuracy.

Also, as the sixth embodiment, in the concentration measuring device according to any of the first embodiment to the fifth embodiment, the concentration measuring device may have the following configuration. It is further provided with a reference light receiving part receiving a part of light, which is irradiated to the subject, through a reference subject that has water as a main component. The absorbance calculation part calculates an absorbance of the subject that cancelled the absorbance related to the water by using an output signal from the light receiving part and an output signal from the reference light receiving part.

According to the sixth embodiment, the reference light receiving part receives a part of light of the irradiation part, which is irradiated to the subject, through a reference subject that has water as a main component. And, the absorbance calculation part calculates an absorbance of the subject that cancelled the absorbance related to the water by using an output signal from the light receiving part and an output signal from the reference light receiving part. In this configuration, the absorbance of the subject that cancelled the absorbance related to the water can be calculated. Therefore, it becomes possible to use the measuring light in the wavelength region where the absorption of water is large.

PREFERRED EMBODIMENTS OF THE INVENTION

Hereinafter, the preferred embodiments of the present invention will be described in reference to the drawings. However, needless to say, an embodiment that the present invention is applicable is not limited to these embodiments described below.

1. First Embodiment

1-1. Configuration

Figure 1:
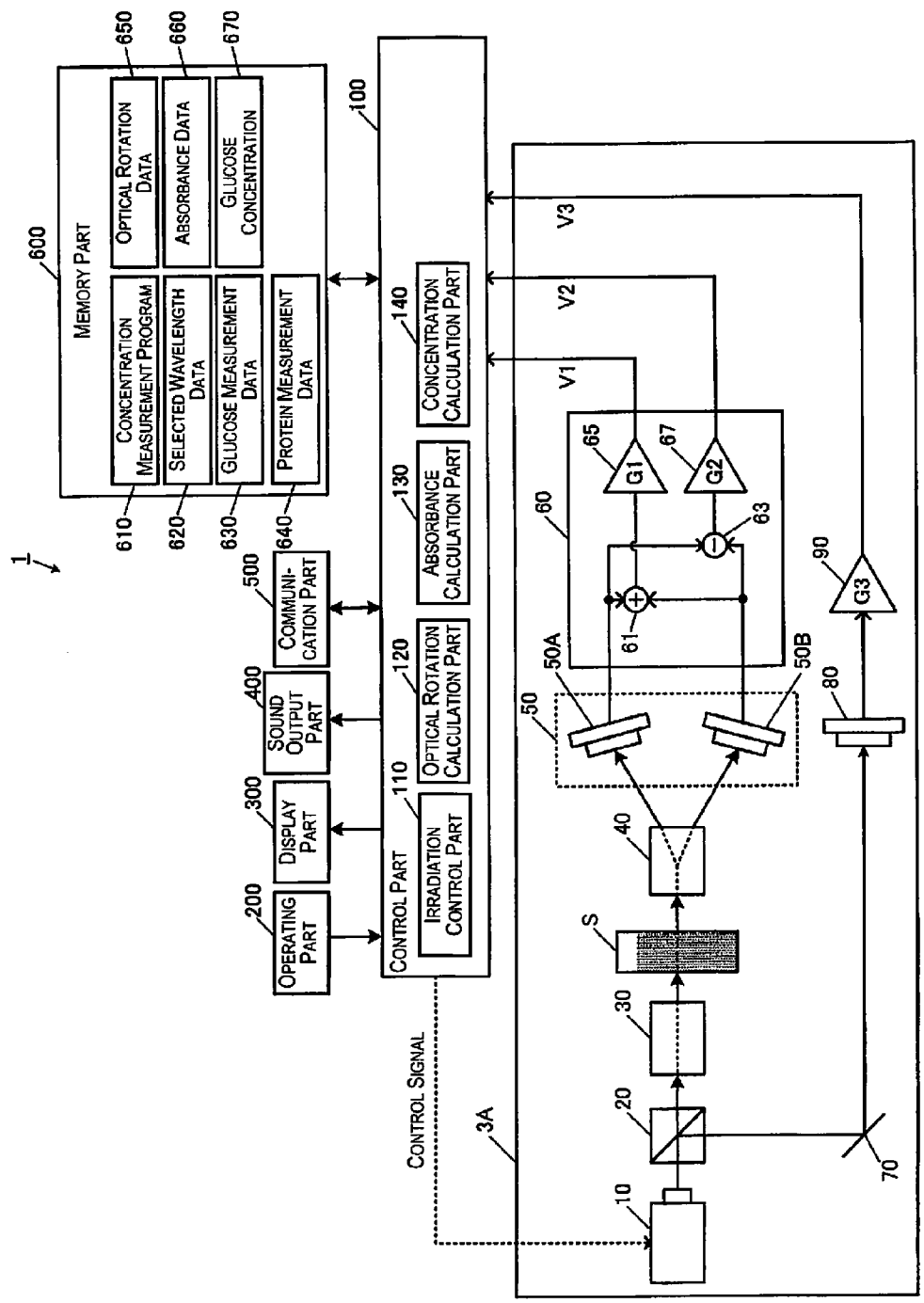
FIG. 1 is a block diagram showing an example of a functional configuration of a concentration measuring device.

FIG. 1 is a block diagram showing an example of a functional configuration cola concentration measuring device 1 in the first embodiment. As a main constituent, the concentration measuring device 1 is configured by a first optical apparatus 3A, a control part 100, an operating part 200, a display part 300, a sound output part 400, a communication part 500, and a memory part 600.

The first optical apparatus 3A is configured by a light source 10, a bifurcation part 20, a polarization part 30, an orthogonal separation part 40, a light receiving part 50, an amplifier 60, a mirror 70, a second light receiving part 80, and a second amplifier 90.

A subject S is placed between the polarization part 30 and the orthogonal separation part 40. The subject includes optically active substance, and it is possible to be an optional sample of a solid, liquid, and the like having an optical transparency. In the present embodiment, the subject S will be described as a test reagent including water, glucose (first component), and protein (second component) that simulate a subcutaneous tissue of an organism. Also, among them, the protein will be described as albumin and globulin that are two types of blood proteins abundantly included as other than blood corpuscle components in blood. This is the situation to measure a glucose concentration in interstitial fluid exuded in the tissue of the body from blood.

The light source 10 is an irradiation part having a configuration to generate and irradiate measuring light in a plurality of wavelengths. For example, it is configured as multiwavelength light source. Under the control of the control part 100, the light source 10 generates and irradiates the measuring light in a wavelength instructed by an irradiation control part 11.

The bifurcation part 20 is a brancher to bifurcate the measuring light irradiated from the light source 10 into two lights between transmitted light and reflected light. For example, it is configured by a beam splitter. The transmitted light from the bifurcation part 20 enters the polarization part 30, and the reflected light is optically guided to the mirror 70.

The polarization part 30 is a polarizing element (polarizer) to transform the outgoing light from the bifurcation part 20 into a linearly polarized light. As the polarization part 30, for example, Glan-Thompson prism, which is a Glan-type polarizer, may be applied.

The orthogonal separation part 40 is an optical element to separate the transmitted light, which is the linearly polarized light transmitted through the subject S, into orthogonal component, that is, polarization component which is 90 degree different. As the orthogonal separation part 40, for example, the Wollaston prism may be applied.

The light receiving part 50 is an element to receive light orthogonally separated by the orthogonal separation part 40, and it is configured by a light detector such as a photodiode, and the like. The light receiving part 50 is configured by a P polarized light receiving part 50A and a S polarized light receiving part 50B, and it receives the polarized light components (P component and S component) which are orthogonally separated by the orthogonal separation part 40 and are orthogonal to each other. A photoelectrical conversion is performed for the light received in the light receiving part 50, and a voltage value corresponding to the light receiving quantity is outputted to the amplifier 50. In the description below, it will describe that a voltage that the photoelectric conversion is performed in the P polarized light receiving part 50A is called as "P polarized light voltage", and a voltage that the photoelectric conversion is performed in the S polarized light receiving part 50B is called as "S polarized light voltage".

The amplifier 60 is an operation part to amply a difference and sum of a light receiving level in the light receiving part 50, and it is configured by an adder 61, a subtracter 63, an amplifier for adder 65, and an amplifier for subtracter 67. The outputs from the P polarized light receiving part 50A and the S polarized light receiving part 50B are respectively added and subtracted in the adder 61 and the subtracter 63, and they are respectively amplified in the amplifier for adder 65, and the amplifier for subtracter 67.

In the present embodiment, it describes that an amplification factor of the amplifier for adder 65 is defined as a first amplification factor "G1", and an amplification factor of the amplifier for subtracter 67 is defined as a second amplification factor "G2". The amplifier 60 outputs a voltage corresponding to a difference of the light receiving level and a voltage corresponding to a sum of the light receiving level to the control part 100. In the description below, it will describe that the voltage corresponding to the difference of the light receiving level is called as "subtraction output voltage", and the voltage corresponding to the sum of the light receiving level is called as "addition output voltage".

The mirror 70 reflects one of the light among the light bifurcated by the bifurcation part 20, and it is guided to the second light receiving part 80.

By the way, in the present embodiment, it is drawn and described as that the light bifurcated in the bifurcation part 20 is guided to the second light receiving part 80 by the mirror 70, but in addition to that, a light path to guide the light bifurcated in the bifurcation part 20 to the second light receiving part 80 may be configured by using a light guide such as an optical fiber.

The second light receiving part 80 receives the measuring light reflected in the mirror 70. The photoelectric conversion is performed for the light received in the second light receiving part 80, and a voltage value corresponding to the light receiving quantity is outputted to the second amplifier 90.

The second amplifier 90 is an amplifier to amplify a voltage outputted from the second light receiving part 80 in a predetermined amplification factor. In the present embodiment, the amplification factor of the second amplifier 90 will be described as the third amplification factor "G3".

A light path from the bifurcation part 20 to the second amplifier 90 is a light path designed as an object to measure an optical rotation and an absorbance at the same time. That is, the light path is designed based on the theory of a double beam method.

The control part 100 is a control device to totally control each part of the concentration measuring device 1. It is a type of computer that is configured by a microprocessor such as the Central Processing Unit (CPU), the Digital Signal Processor (DSP), and the like, or the Application Specific Integrated Circuit (ASIC), and the like.

As a main functional part, the control part 100 is provided with an irradiation control part 110, an optical rotation calculation part 120, an absorbance calculation part 130, and a concentration calculation part 140. However, these functional parts are disclosed as one embodiment so that these all functional parts are not always essential components. Also, other functional parts may be added as an essential component.

The irradiation control part controls the irradiation of measuring light to the subject S by the light source 10. Specifically, a control signal for instructing a wavelength of the measuring light is outputted to the light source 10 so as to control the light source 10 to generate and irradiate the measuring light in a desired wavelength.

An optical rotation calculation part 120 calculates an optical rotation of the subject S by using an output voltage (output signal) from the amplifier 60.

The absorbance calculation part 130 calculates an absorbance of the subject S by using an output voltage (output signal) from the amplifier 60 and an output voltage (output signal) of the second amplifier 90.

The concentration calculation part 140 calculates a glucose concentration in the subject S by using a glucose measurement data 630 (first measurement data) related to an aqueous solution of simple glucose, a protein measurement data 640 (second measurement data) related to an aqueous solution of simple protein, an optical rotation calculated by the optical rotation calculation part 120, and an absorbance calculated by the absorbance calculation part 130.

The operating part 200 is an input device configured by button switches, and the like, and outputs a signal of a pressed button to the control part 100. By the operation of this operating part 200, various instruction inputs such as an instruction to start measurement of a glucose concentration, and the like are performed.

The display part 300 is configured by the Liquid Crystal Display (LCD), and is a display device to perform various displays based on a display signal inputted from the control part 100. In the display part 300, information such as a measuring value of glucose concentration is displayed.

The sound output part 400 is a sound output device to perform various sound outputs based on a sound output signal inputted from the control part 100. For example, it outputs an auditory signal such as a measurement start, a measurement end, an occurrence of an error, and the like.

A communication part 500 is a communication device to send and receive information, which is used in the internal device, with an external information processing device in accordance with the control of the control part 100. As a communication system of the communication part 500, various systems such as a system wiring through a cable with a prescribed communication standard, a system connecting through intermediate equipment that has dual purpose with a battery charger so-called cradle, a system wirelessly connecting by using a near field communication, and the like are applicable.

The memory part 600 is configured by a memory device such as a Read Only Memory (ROM) or a flash ROM, Random Access Memory (RAM), and the like. The memory part 600 stores various programs, data, and the like to realize various functions such as a system program of the concentration measuring device 1, an optical calculation function, an absorbance calculation function, and the like. Also, it has a work area to temporary store data during processing of various processes, a processing result, and the like.

In the memory part 600, a concentration measurement program 610 read by the control part 100 and executed as a concentration measuring process (see FIG. 5) is stored. The concentration measuring process will be described in detail later.

Also, a selected wavelength data 620, a glucose measurement data 630, a protein measurement data 640, an optical rotation data 650, an absorbance data 660, and a glucose concentration 670 are stored in the memory part 600. These data are described later.

1-2. Principle 1-2-1. Principle of Measurement of Glucose Concentration

Figure 2A:
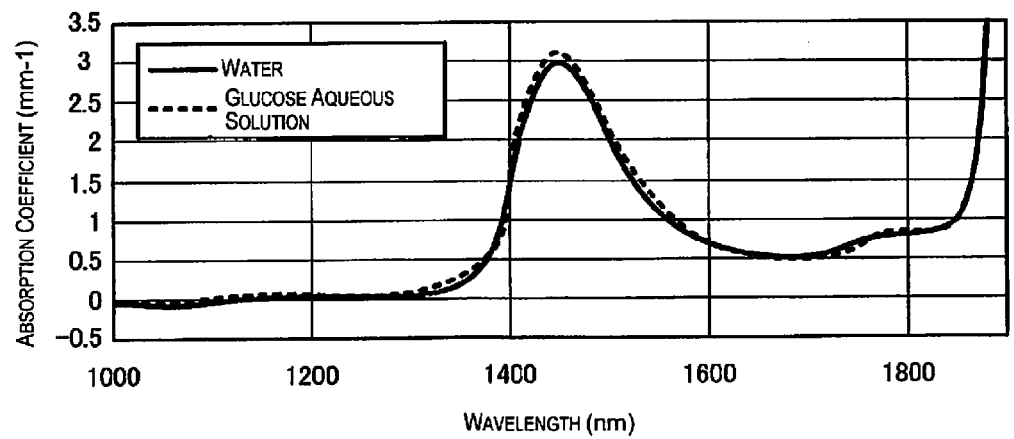
FIG. 2A is an illustration showing an example of a wavelength dependence of absorption coefficient for water and glucose aqueous solutions.

FIG. 2A is an illustration showing an example of a result of an experiment that measures an absorption spectrum of water and glucose aqueous solutions. In FIG. 2A, the horizontal axis is a wavelength of measuring light (the unit is nm (nanometer)), and the vertical axis is an absorption coefficient (the unit is $mm^{-1}$). In here, as a glucose aqueous solution, it shows a wavelength dependence of absorption coefficient of a glucose aqueous solution that 9.4 g (gram) per 1 dl (deciliter) glucose is dissolved in water.

As shown in the drawing, the absorption coefficient of water in the wavelength region until approximately 1300 nm is almost zero, but when it is exceeded, the absorption coefficient of water tends to be larger. Also, it is understood that a curve indicating the absorption coefficient of glucose aqueous solution and a curve indicating the absorption coefficient of water are almost overlapped. When the subject S as an organism that is a subcutaneous tissue of an organism in more detail is considered, a blood concentration of glucose is approximately 80 to 100 [mg/dl] in an able-bodied person. That is, the glucose concentration of the glucose aqueous solution used in this experiment corresponds to approximately 100 times of the glucose concentration in the blood. Accordingly, the absorbance of water is much larger than the absorbance of glucose when they are compared, and when the glucose concentration of organism is measured as the subject S, the water interferes the measurement so that it becomes a factor that the accuracy of the glucose concentration measurement becomes lower.

Figure 2B:
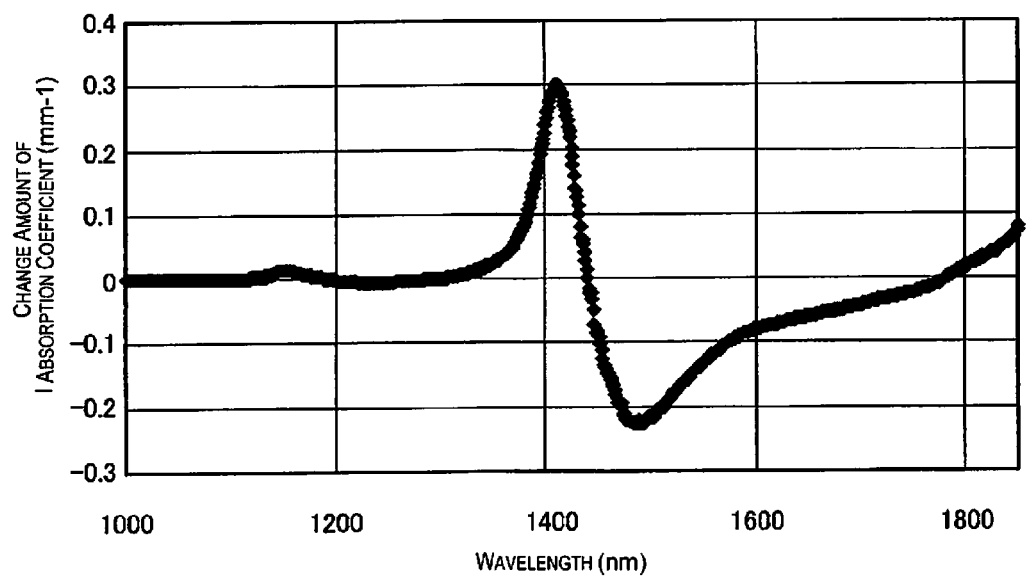
FIG. 2B is an illustration showing an example of a wavelength dependence of a change amount of absorption coefficient for water.

FIG. 2B is an illustration showing an example of a result of an experiment that checks temperature dependence of an absorbance of water. In FIG. 2B, the horizontal axis is a wavelength of measuring light (the unit is nm), and the vertical axis is a change amount of an absorption coefficient (the unit is $mm^{-1}$). It is an illustration showing plots depending on a wavelength of measuring light such as an absorption coefficient of water in the case that the water temperature is 38° C., and a difference with the absorption coefficient of water in the case that the water temperature is 22.8° C. as the change amount of the absorption coefficient. That is, the temperature change of water is approximately 15° C., and the change amount of the absorption coefficient is examined.

As shown in the drawing, it is understood that the change amount of absorption coefficient of water increases from the wavelength of approximately 1350 nm, and the wavelength value becomes a maximum at the vicinity of 1400 nm. After that, after the change amount of absorption coefficient was reduced and passed zero point, the value of the wavelength becomes a minimum at the vicinity of 1500 nm. And, as the wavelength becomes longer from this point, the change amount of absorption coefficient increases gradually. That is, in the near infrared wavelength region, it is understood that the temperature dependence of absorption of water is large.

According to these experimental results, the absorption of water greatly affects to the measurement of glucose concentration, and this becomes a main factor that the measurement accuracy of the glucose concentration becomes lower. Thus, the present inventors have considered that the glucose concentration is measured by irradiating the measuring light in the wavelength region of which the absorbance related to the water in the subject can be practically ignored, and by using the optical rotation and the absorbance of the subject, which were calculated at this time, together. Based on the experimental result of FIG. 2, in the present embodiment, it is described as that the wavelength region where the absorbance related to the water in the subject can be practically ignored is in the wavelength region of 400 nm to the vicinity of 1300 nm.

In the present specification, when a vicinity of one wavelength is mentioned, it does not have to be the precise wavelength. For example, it means that the wavelength includes within a range of approximately 1% of the wavelength. For example, when a vicinity of 1300 nm is mentioned, it means that the wavelength includes within a range of approximately 1% of 1300 nm. In this range, it can obtain the same effect. Hereinafter, a calculation method of glucose concentration in the present embodiment, and a selection method of a wavelength of the measuring light used in the calculation of glucose concentration will be described in detail.

(1) Calculation of Glucose Concentration

In the present embodiment, the calculation of glucose concentration is realized by performing a predetermined multivariate analysis by using a glucose measurement data (first measurement data), a protein measurement data (second measurement data) related to an aqueous solution of a simple protein, an optical rotation calculated by the optical rotation calculation part 120, and an absorbance calculated by the absorbance calculation part 130.

As described above, in the present embodiment, albumin and globulin are simulated as protein so that in the explanation of principle below, it is described in the case that a concentration of total three components of glucose, albumin and globulin is calculated.

In the present embodiment, as the multivariate analysis, it performs to solve the predetermined simultaneous equations related to an optical rotation and an absorbance. Specifically, the multivariate analysis is performed as the concentrations of glucose, albumin and globulin to be unknown. The unknown concentrations are three so that at least three linear combination formulas are simultaneously set. Therefore, a concentration of each component can be calculated.

Further, in the present embodiment, it is characterized in that a concentration is calculated by using an optical rotation and an absorbance together. Thus, a linear combination formula related to the optical rotation and a linear combination formula related to the absorbance are combined and the simultaneous equation is completed. Specifically, when the simultaneous equation is completed by three linear combination formulas, it may be any one of the cases that one linear combination formula related to the optical rotation and two linear combination formulas related to the absorbance are combined or two linear combination formulas related to the optical rotation and one linear combination formula related to the absorbance are combined.

As an example, a simultaneous equation that one linear combination formula related to an optical rotation and two linear combination formulas related to an absorbance are combined is shown in Equation (1).

[Equation (1)]

$$\begin{cases} a_1 X + b_1 Y + c_1 Z = \alpha \\ d_2 X + e_2 Y + f_2 Z = \beta \\ d_3 X + e_3 Y + f_3 Z = \gamma \end{cases} \quad (1)$$

In Equation (1), the first formula is a linear combination formula related to an optical rotation. Also, the second and third formulas are linear combination formulas related to an absorbance. In Equation (1), unknowns are represented by "X", "Y", and "Z". They are the concentrations (the unit is g/dl) of glucose, albumin and globulin, respectively. In the right-hand value, the value "$\alpha$" is a calculation value of an optical rotation in the wavelength "$\lambda_1$", the value "$\beta$" is a calculation value of an absorbance in the wavelength of "$\lambda_2$", and the value "$\gamma$" is a calculation value of an absorbance in the wavelength of "$\lambda_3$". These values are values respectively calculated by the optical rotation calculation part 120 and the absorbance calculation part 130 when the measuring light in each wavelength is irradiated to the subject S. That is, it is the observation values of the optical rotation and the absorbance.

The values "$a_1$", "$b_1$", and "$c_1$" are specific rotations of glucose, albumin and globulin in the wavelength "$\lambda_1$", respectively. The values "$d_2$", "$e_2$", and "$f_2$" are an absorbance per 1 g/dl of glucose, albumin and globulin in the wavelength "$\lambda_2$", respectively. Also, the values "$d_3$", "$e_3$", and "$f_3$" are an absorbance per 1 g/dl of glucose, albumin and globulin in the wavelength "$\lambda_3$", respectively. These values are preliminary stored in the memory part 600 as physical properties defined by every wavelength of the measuring light and a measurement data related to an aqueous solution of each simple component.

More specifically, a glucose measurement data 630 that defines a specific rotation in different wavelengths and an absorbance per unit concentration are stored in the memory part 600. Also, a protein measurement data 640 that defines specific rotations of albumin and globulin in different wavelengths and an absorbance per unit concentration is stored in the memory part 600.

When Equation (1) is rewritten into a matrix form, it becomes Equation (2) as follows.

[Equation (2)]

$$\begin{pmatrix} a_1 & b_1 & c_1 \\ d_2 & e_2 & f_2 \\ d_3 & e_3 & f_3 \end{pmatrix} \begin{pmatrix} X \\ Y \\ Z \end{pmatrix} = \begin{pmatrix} \alpha \\ \beta \\ \gamma \end{pmatrix} \quad (2)$$

Equation (2) can be solved as Equation (3) below.

$$\begin{pmatrix} X \\ Y \\ Z \end{pmatrix} = \begin{pmatrix} a_1 & b_1 & c_1 \\ d_2 & e_2 & f_2 \\ d_3 & e_3 & f_3 \end{pmatrix}^{-1} \begin{pmatrix} \alpha \\ \beta \\ \gamma \end{pmatrix} \quad (3)$$

$$= \begin{pmatrix} A_1 & B_1 & C_1 \\ A_2 & B_2 & C_2 \\ A_3 & B_3 & C_3 \end{pmatrix} \begin{pmatrix} \alpha \\ \beta \\ \gamma \end{pmatrix}$$

Accordingly, the glucose concentration "X" can be obtained as Equation (4) below. [Equation (4)]

$$X = A_1 \cdot \alpha + B_1 \cdot \beta + C_1 \cdot \gamma \quad (4)$$

Equation (1) is a simultaneous equation that a linear combination formula related to an optical rotation and a linear combination formula related to an absorbance are combined. By the experiments, the present inventors have confirmed that for the respective optical rotation and absorption, the optical rotation and the absorbance of the subject, which were measured, are presented in a linear combination of the optical rotation and the absorbance in each component of the subject, respectively. Thus, a relational expression presenting the optical rotation of the subject S that is presented in a linear combination of an optical rotation in each component, and a relational expression presenting the absorbance of the subject S that is presented in a linear combination of an absorbance in each component are respectively defined. By setting up a simultaneous equation for these relational expressions, a concentration of each component included in the subject S is calculated.

There is a reason to calculate a concentration by using an optical rotation and an absorbance in this way. That is, for example, when it considers that the subject S is measured as an organism, realistically, it is impossible to perform the measurement in an environment without any temperature fluctuation. When there is a temperature fluctuation, by the experiments, it has become clear that the measurement accuracy of the concentration is dramatically improved in the case that a concentration is calculated by using an optical rotation and an absorbance together compare to in the case that the measurement is performed by using a single optical rotation or a single absorbance, respectively.

It will be described specifically. The present inventors have conducted the experiments to calculate a glucose concentration in the method that a glucose concentration is calculated by using an absorption only (hereafter referred to as "absorption method"), and the method that a glucose concentration is calculated by using an optical rotation and an absorption (hereinafter referred to as "optical rotation and absorption method") based on the method of multivariate analysis by using the above simultaneous equations. Also, in the respective methods, the experiments that determine quantity how much error of the measurement results of the concentrations is superimposed have been conducted.

Figure 3A:
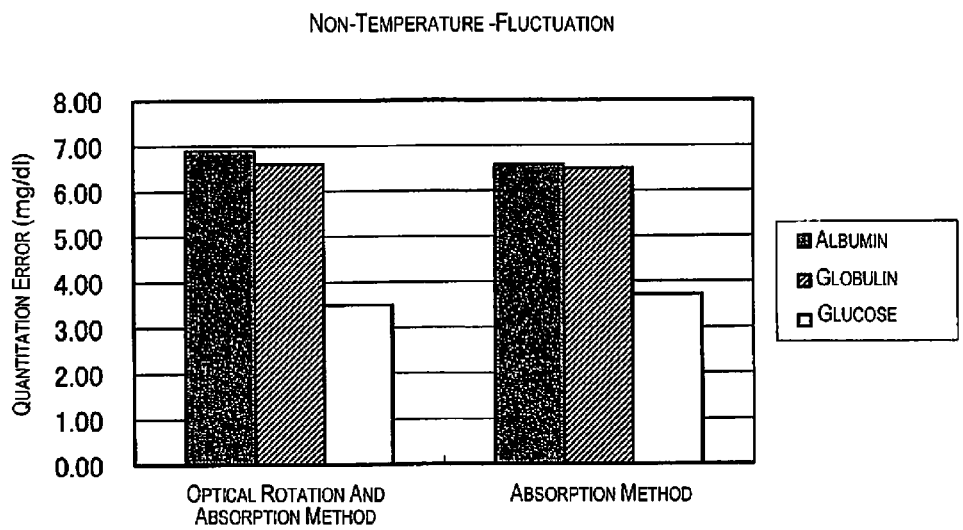
FIG. 3A is a bar chart showing a quantitation error of a glucose concentration in the case that there is no temperature fluctuation.
Figure 3B:
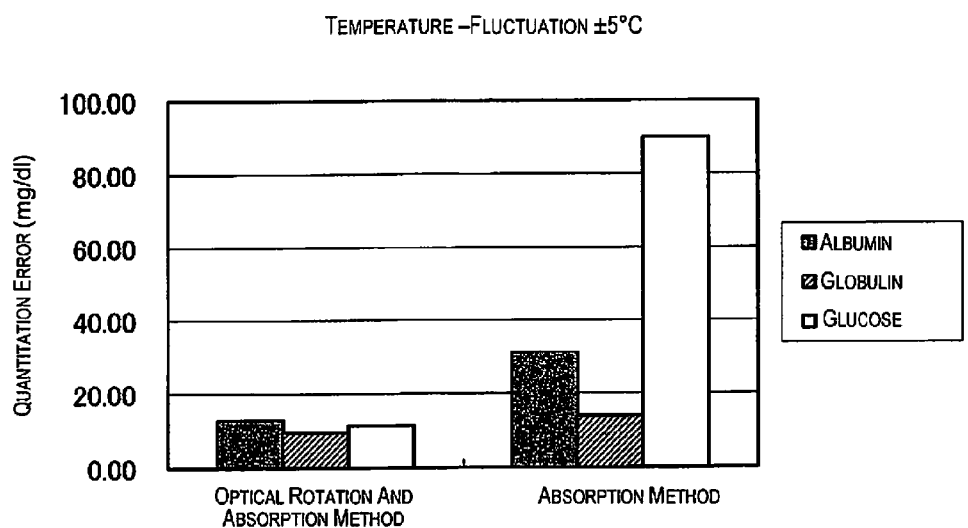
FIG. 3B is a bar chart showing a quantitation error of a glucose concentration in the case that there is a temperature fluctuation.

FIG. 3 is an illustration showing examples of the experimental results. FIG. 3A is an illustration showing an example of the experimental results that have been conducted to check a quantitation error of a glucose concentration in the state that the temperature fluctuation does not occur with respect to a certain based temperature (e.g., 38° C.). On the other hand, FIG. 3B is an illustration showing an example of the experimental results that have been conducted to check a quantitation error of a glucose concentration in the state that the temperature fluctuation is ±5° C. of a certain based temperature (there is a temperature fluctuation).

The respective drawings shows a bar chart estimating a quantitation error of a glucose concentration "X", an albumin concentration "Y", and a globulin concentration "Z" in the optical rotation and absorption method and the absorption method respectively. The vertical axis indicates the quantitation error (the unit is mg/dl), and as the height of the bar charge is higher, it means that the large error is included by the calculated concentration.

As shown in the experimental results, under the experimental environment that does not have any temperature fluctuation, it is understood that there is almost no quantitation error in the optical rotation and absorption method and the absorption method. However, when there is a temperature fluctuation, the significant difference in the quantitation error is presented. Specifically, as shown in FIG. 3B, in the absorption method, the quantitation error of glucose is approximately 90 mg/dl that is very large value so that it is understood that this level of error is hard to endure for the practical use. However, in the optical rotation and absorption method, the quantitation error of the glucose concentration is approximately one-tenth compare to the case of the absorption method.

When a glucose concentration of an organism, more specifically, a subcutaneous tissue of an organism as the subject S is measured, it is hard to perform the measurement without any influence of the temperature fluctuation. That is, the subcutaneous tissue is close to the surface of the organism so that it is easy to get influenced by the outside temperature, and also, it is still more influenced when the measurement target portion is a peripheral portion such as a fingertip, an earlobe, and the like. The measurement is performed by contacting a probe provided with the first optical apparatus 3A without the optical source 10 to the measurement target portion, and the contacted portion is blocked out from the outside temperature so that the temperature of the measurement target portion may be changed by the body temperature during the measurement. From the experimental results of FIG. 3, it is understood that the optical rotation and absorption method is appropriate to perform the measurement of a concentration.

(2) Selection of Wavelength

FIG. 4 is an explanatory illustration showing a wavelength of measuring light. The present inventors have combined wavelengths belonging to the wavelength region of 400 nm to 2000 nm in a round-robin, and an experiment that measures a glucose concentration in the optical rotation and absorption method is performed. Then, a histogram is provided for a frequency of a wavelength in the combinations that an error (quantitation error) of the calculated glucose concentration was less than a certain level. For example, when an error of the measured glucose concentration by using the combination of three wavelengths of 400 nm, 410 nm, and 700 nm was less than a certain level, one is added for the respective frequencies in the three wavelengths of 400 nm, 410 nm, and 700 nm. In this way, the histogram is provided.

In the optical rotation and absorption method, a glucose concentration is calculated in accordance with the simultaneous equation of Equation (1). As described above, Equation (1) is the simultaneous equation that combines a linear combination formula related to the optical rotation and a linear combination formula related to the absorption. In the present experiment, a wavelength applied to the linear combination formula related to the optical rotation and a wavelength applied to the linear combination formula related to the absorption are classified, and the histograms in different wavelengths for the wavelength applied to the linear combination formula related to the absorption and the wavelength applied to the linear combination formula related to the optical rotation are provided, respectively.

Figure 4A:
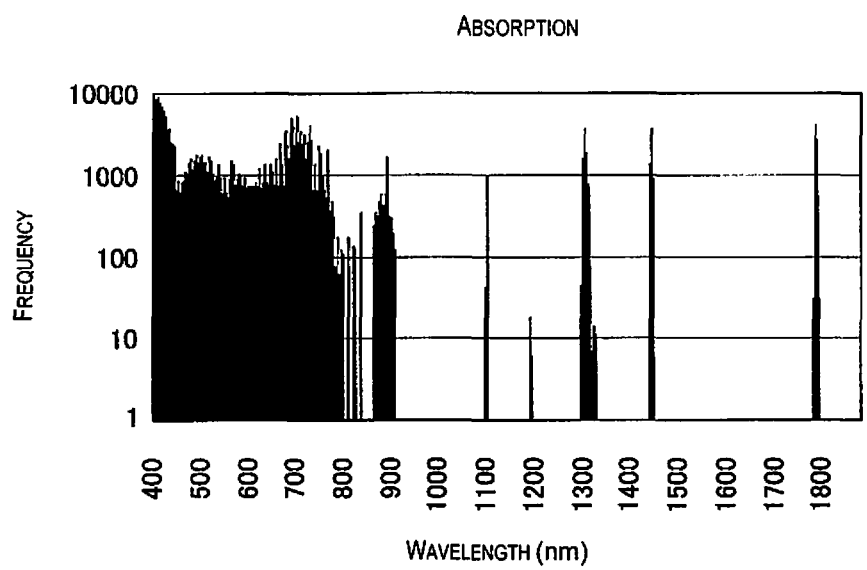
FIG. 4A is a histogram showing an error related to absorption of light.
Figure 4B:
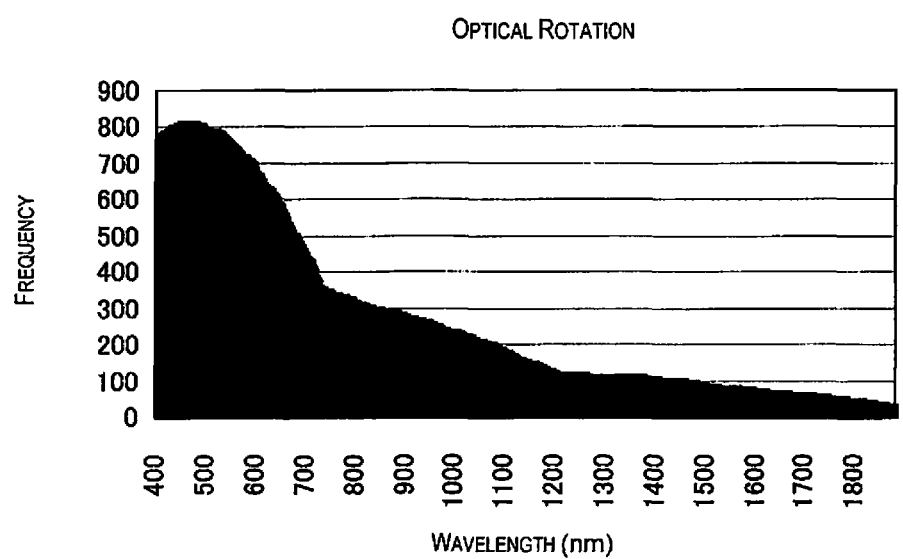
FIG. 4B is a histogram showing an error related to an optical rotation.

The histogram related to the absorption is shown in FIG. 4A, and the histogram related to the optical rotation is shown in FIG. 4B. In the respective drawings, the horizontal axis indicates a wavelength (the unit is nm), and the vertical axis indicates a frequency of appearance. When the wavelength has a higher frequency of appearance, this means that it is the wavelength that the quantitation error of the glucose concentration is small (that is, it is an appropriate wavelength for a measurement).

As shown in the histograms in FIG. 4A and FIG. 4B, when it is closer to the shorter wavelength side, it is understood that there exists the wavelength region including many high frequency wavelengths. However, as shown in the histogram in FIG. 4A and FIG. 4B, there is a difference between them. As shown in the histogram related to the absorption in FIG. 4A, the frequency is high in the wavelength region of 400 nm to 900 nm, and also, even in the higher wavelength side, it is understood that many wavelength regions having a high frequency are existed. As described above, in the present embodiment, the wavelength region that the absorbance related to water in the subject can be practically ignored is the wavelength region of 400 nm to the vicinity of 1300 nm, and the measuring light in this wavelength region is irradiated to the subject.

Thus, for the absorption, any of the wavelength regions of 400 nm to 900 nm, the vicinity of 1100 nm, the vicinity of 1190 nm, and the vicinity of 1300 nm is defined as an absorbance error reducing wavelength region based on the absorption histogram in FIG. 4A, and a wavelength of the measuring light (hereinafter referred to as "measuring light for absorbance") to be used for the calculation of the absorbance is selected among the absorbance error reducing wavelength regions.

Also, as shown in the histogram related to the optical rotation in FIG. 4B, the frequency of appearance is high when it is closer to the lower wavelength side so that it is understood that the quantitation error of the glucose concentration tends to be small. Thus, for the optical rotation, the wavelength regions 400 nm to 800 nm is defined as an optical rotation error reducing wavelength region based on the optical rotation histogram in FIG. 4B, and a wavelength of the measuring light (hereinafter referred to as "measuring light for optical rotation") to be used for the calculation of the optical rotation is selected among the optical rotation error reducing wavelength regions.

1-2-2. Calculation Method of Optical Rotation

The light amount of transmitted light that transmitted through the subject S is "$E_a^2$". An incidence angle of linear polarized light to the orthogonal separation part 40 is "$\theta_0$". An optical rotation (angle of rotation) in the subject S is "$\theta$". At this point, an electric field of P polarized light and an electric field of S polarized light are represented as "$E_a \times \cos(\theta+\theta_0)$" and "$E_a \times \sin(\theta+\theta_0)$", respectively. Accordingly, the electric field of a P polarized light voltage and the electric field of a S polarized light voltage are represented as "$E_a^2 \times \cos^2(\theta+\theta_0)$" and "$E_a^2 \times \sin^2(\theta+\theta_0)$", respectively.

At this point, a subtraction voltage "Vs" can be obtained as Equation (5) by subtracting the S polarized voltage from the P polarized voltage. Also, an adder voltage "Va" can be obtained as Equation (6) by adding the S polarized voltage and the P polarized voltage.

[Equation 5]

$$Vs = E_a^2 \cos^2(\theta+\theta_0) - E_a^2 \sin^2(\theta+\theta_0) \quad (5)$$
$$= E_a^2(\cos^2(\theta+\theta_0) - \sin^2(\theta+\theta_0))$$

[Equation 6]

$$Va = E_a^2 \cos^2(\theta+\theta_0) + E_a^2 \sin^2(\theta+\theta_0) \quad (6)$$
$$= E_a^2(\cos^2(\theta+\theta_0) + \sin^2(\theta+\theta_0))$$
$$= E_a^2$$

The amplifier 60 computes the subtraction voltage "Vs" and the adder voltage "Va" represented by Equation (5) and Equation (6), and amplifies the computed results, respectively. An amplification factor for the subtraction voltage "Vs" is the first amplification factor "G1", and an amplification factor for the adder voltage "Va" is the second amplification factor "G2" so that a subtraction output voltage "V1" and an adder output voltage "V2" outputted from the amplifier 60 is set as Equation (7) and Equation (8), respectively.

[Equation (7)]

$$V1 = G1 \cdot Vs \quad (7)$$
$$= G1 \cdot E_a^2(\cos^2(\theta+\theta_0) - \sin^2(\theta+\theta_0))$$

[Equation (8)]

$$V2 = G2 \cdot Va \quad (8)$$
$$= G2 \cdot E_a^2$$

Equation (9) can be derived from Equation (7) and Equation (8).

[Equation (9)]

$$\frac{G2}{G1} \frac{V1}{V2} = \cos^2(\theta+\theta_0) - \sin^2(\theta+\theta_0) \quad (9)$$
$$= \cos 2(\theta+\theta_0)$$

Accordingly, the optical rotation " " can be calculated as Equation (10) from Equation (9).

[Equation (10)]

$$\theta = \frac{1}{2}\arccos\left(\frac{G2}{G1}\frac{V1}{V2}\right) - \theta_0 \quad (10)$$
$$= \frac{1}{2}\arccos\left(\frac{1}{C1}\frac{V1}{V2}\right) - \theta_0$$

However, it was replaced to "G1/G2=C1".

1-2-3. Calculation Method of Absorbance

An amount of light received in the second light receiving part 80 is "$E_b^2$". At this point, an output voltage "V3" from the second amplifier 90 is given in Equation (11).

[Equation 11]

$$V3 = G3 \cdot E_b^2 \quad (11)$$

In this case, the absorbance "Abs" can be calculated as Equation (12) by using the adder output voltage "V2" and the output voltage "V3".

[Equation (12)]

$$\begin{aligned}\text{Abs} &= -\log_{10}\frac{E_a^2}{E_b^2} \quad (12)\\ &= -\log_{10}\frac{G3\cdot V2}{G2\cdot V3}\\ &= -\left(\log_{10}\frac{V2}{V3} + \log_{10}\frac{G3}{G2}\right)\\ &= -\left(\log_{10}\frac{V2}{V3} + \log_{10}C2\right)\end{aligned}$$

However, it was replaced to "G3/G2=C2".

1-2-4. Calibration of Optical Apparatus

In the present embodiment, an optical apparatus is calibrated so as to calculate an optical rotation and an absorbance properly.

For the calculation of the optical rotation "θ", two parameter values of "C1" and "$\theta_0$" are required. It is possible to calculate the value "C1" by using a design value of the "G1" and a design value of the "G2". Also, the value "$\theta_0$" is mechanically set in a predetermined angle. However, to calculate an optical rotation presented in an extremely small angle, the above parameter values governs whether the calculation of the optical rotation is properly performed.

In an amplification factor to the design of the amplifier 60, it may include an error caused by an accuracy of a utilized element, and the like. It may be considered that the measurement accuracy of the optical rotation is lowered by the error. Thus, more than two substances that an optical rotation is known are measured as a measurement target, and in this case, the optical rotation is calculated by using a voltage value outputted from the optical apparatus. Then, the optical apparatus is calibrated based on the deviation from a theoretical value of the optical rotation of the substances used as the calculated value of the optical rotation and the measurement target. There are two of "C1" and "$\theta_0$" so that when more than two equations are set, two unknowns are solved. The solution of an equation can be calculated by using, for example, publicly known numeric operation such as least square, and the like.

In the same manner, a parameter related to the calculation of the absorbance is obtained. Specifically, two parameter values of a ratio "C2" of the second amplification factor "G2" to the third amplification factor "G3" and a ratio "$E_a^2/E_b^2$" of the amount of light "$E_a^2$" to "$E_b^2$" are obtained. In the amplifier factors (design values) of the amplifier 60 and the second amplifier 90, an error caused by the accuracy of the above utilized element and the like may be included. Also, a shimmering in the amount of light received in the light receiving part 50 and the second light receiving part 80 may occur attributable to a characteristic of an optical element configuring an irradiating system and a light receiving system of measuring light. These error factors cause that an accuracy of the absorbance calculation is lowered.

Thus, the measurement is performed in the state that the subject S is not placed (non-existing state of sample), or in the state that a predetermined standard reagent is placed, and an absorbance is calculated by using the voltage value outputted from the optical apparatus in this case. Also, the optical apparatus is calibrated based on the deterioration from the theoretical value of the absorbance of the calculation value of this absorbance and the standard reagent, and the like.

1-3. Flow of Process

Figure 5:
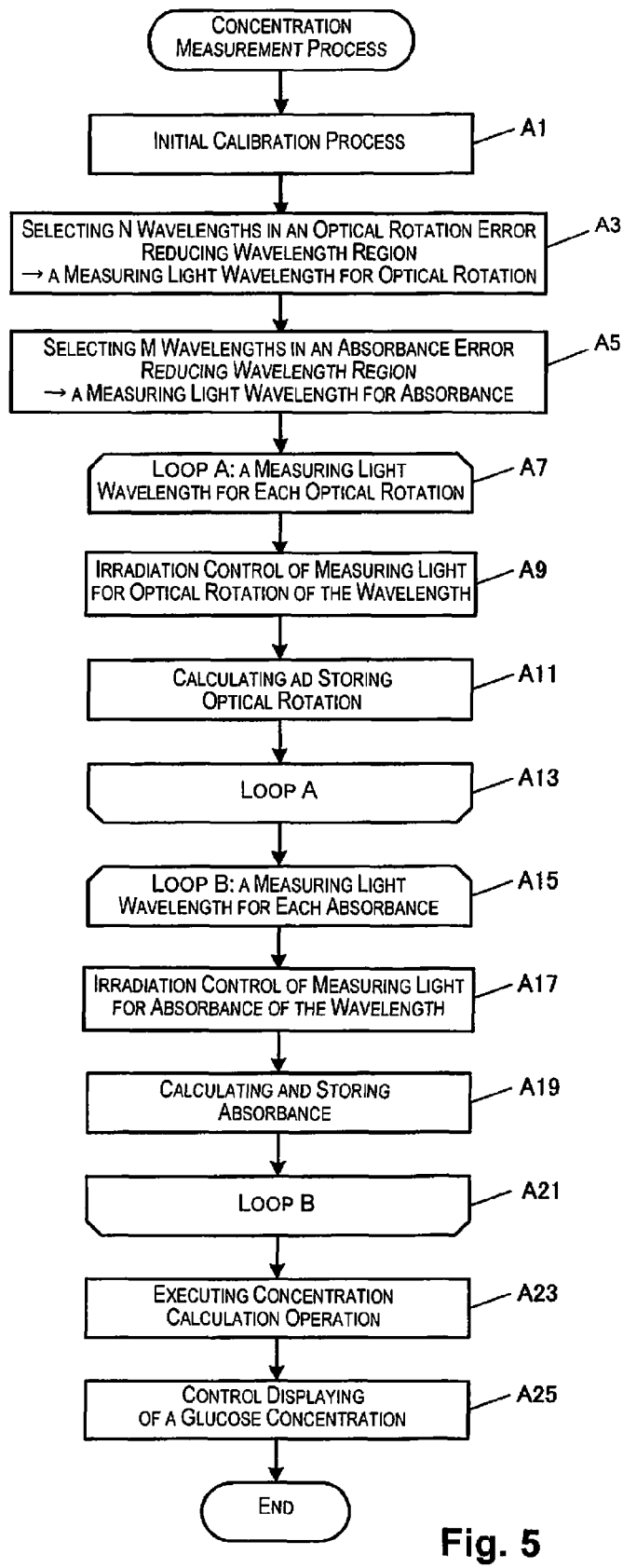
FIG. 5 is a flowchart showing a flow of a concentration measuring process.

FIG. 5 is a flowchart showing a flow of a concentration measurement process that the control part 100 executes in accordance with the concentration measurement program 610 stored in the memory part 600.

First, the control part 100 performs an initial calibration process (Step A1). Specifically, as described above, the optical apparatus is calibrated by obtaining a parameter related to the calculation of an optical rotation and a parameter related to the calculation of an absorbance.

Next, the control part 100 selects N wavelengths (N is an integer of one or more) in the above described optical rotation error reducing wavelength region, and it is stored in the selected wavelength data 620 as a measuring light wavelength for optical rotation (Step A3). Also, the control part 100 selects M wavelengths (M is an integer of one or more) in the above described absorbance error reducing wavelength region, and it is stored in the selected wavelength data 620 as a measuring light wavelength for absorbance (Step A5).

After that, the control part 100 performs a loop A process for a respective measuring light wavelength for each optical rotation (Steps A7 to A13). In the loop A process, the control part 100 performs an irradiation control of the measuring light for optical rotation in the wavelength (Step A9). Specifically, a control signal to generate and irradiate the measuring light for optical rotation in the wavelength is outputted to the light source 10 so as to control the measuring light for optical rotation to be irradiated to the subject S.

Next, the optical rotation calculation part 120 calculates an optical rotation in accordance with Equation (10) by using a value of the parameter determined in the initial calibration process, and an adder output voltage and a subtraction output voltage from the amplifier for adder 65 and the amplifier for subtraction 67, and it is stored in the optical rotation data 650 of the memory part 600 (Step A11). The control part 100 carries out a process of the next measuring light wavelength for optical rotation. When the processes of Step 9 to and Step 11 have been performed for all of the measuring light wavelengths for optical rotation, the control part 100 completes the process of the loop A (Step A13).

After that, the control part 100 performs a loop B process for a respective measuring light wavelength for each absorbance (Step A15 to A21). In the loop B process, the control part 100 performs an irradiation control that the measuring light for absorbance in the wavelength is irradiated to the subject S (Step A17).

Next, the absorbance calculation part 130 calculates an absorbance in accordance with Equation (12) by using a value of the parameter determined in the initial calibration process, an adder output voltage from the amplifier for adder 65, and an output voltage from the second amplifier 90. It is stored in the absorbance data 660 of the memory part 600 (Step A19). The control part 100 carries out a process of the next measuring light wavelength for absorbance. When the process of Step A17 and A19 is performed for all of the measuring light wavelengths for absorbance, the control part 100 completes the process of the loop B (Step A21).

After the loop B, the concentration calculation part 140 executes the concentration calculation operation (Step A23). Specifically, the glucose and protein concentrations are calculated by using the glucose measurement data 630 of the memory part 600, the protein measurement data 640, the calculation optical rotation related to each measuring light wavelength for optical rotation stored in the optical rotation data 650, the calculation absorbance related to each measuring light wavelength for absorbance stored in the absorbance data 660, and by using the method of multivariate analysis as described in the principle.

In this case, when the number of optical rotation and absorbance used for the calculation is more than the number of unknowns, it is in the state of so-called excessive determinations so that an optimized solution of the concentration in each component can be obtained at high speed. That is, in the computer arithmetic processing, a numeric calculation is performed by using a convergence calculation such as, for example, least-square method so that more measured values for using the calculation, it can be swiftly converged and in addition, higher accurate value can be obtained.

After the concentration calculation operation was performed, the control part 100 controls the display part 300 to display the calculated glucose concentration 670 as the measurement result (Step A25). And, the control part 100 completes the concentration measurement process.

1-4. Advantageous Effects

In the concentration measurement device 1, the measuring light in the wavelength region that the absorbance related to water in the subject S can be practically ignored is irradiated to the subject S by the optical source 10. The transmitted light that was transmitted through the subject S is received in the light receiving part 50. The optical rotation calculation part 120 calculates an optical rotation of the subject S by using an output signal from the light receiving part 50, and the absorbance calculation part 130 calculates an absorbance of the subject S by using an output signal from the light receiving part. The concentration calculation part 140 calculates a concentration of glucose by using the glucose measurement data 630 related to the aqueous solution of simple glucose, the protein measurement data 640 related to the aqueous solution of simple protein, an optical rotation calculated by the optical rotation calculation part 120, and an absorbance calculated by the absorbance calculation part 130. The measurement is performed by using the measuring light in the wavelength region that the absorbance related to water in the subject S can be practically ignored, so that the effect by the absorption of water is expelled and it is possible to properly calculate the concentration of the selected component in the subject S.

When it considers that the subject S is an organism (more specifically, a subcutaneous tissue of an organism), the components included in the subject can be simulated as glucose (the first component) and protein (the second component). By conducting the experiments, the present inventors have clarified that it is appropriate to irradiate the measuring light in the optimum wavelength region of 400 nm to the vicinity of 1300 nm. In the further analysis, the wavelength region of 400 nm to 800 nm is irradiated for the measuring light for optical rotation. Any of the wavelength regions of 400 nm to 900 nm, the vicinity of 1100 nm, the vicinity of 1190 nm, and the vicinity of 1300 nm is irradiated for the measuring light for absorbance. It was confirmed that they are appropriate. The measuring light in a selected wavelength among these wavelength regions is irradiated to the subject S, and an optical rotation and an absorbance are calculated. A concentration is calculated by using a method of multivariate analysis so that it becomes possible to improve the measurement accuracy of a concentration compare to the conventional method.

2. Second Embodiment

Figure 6:
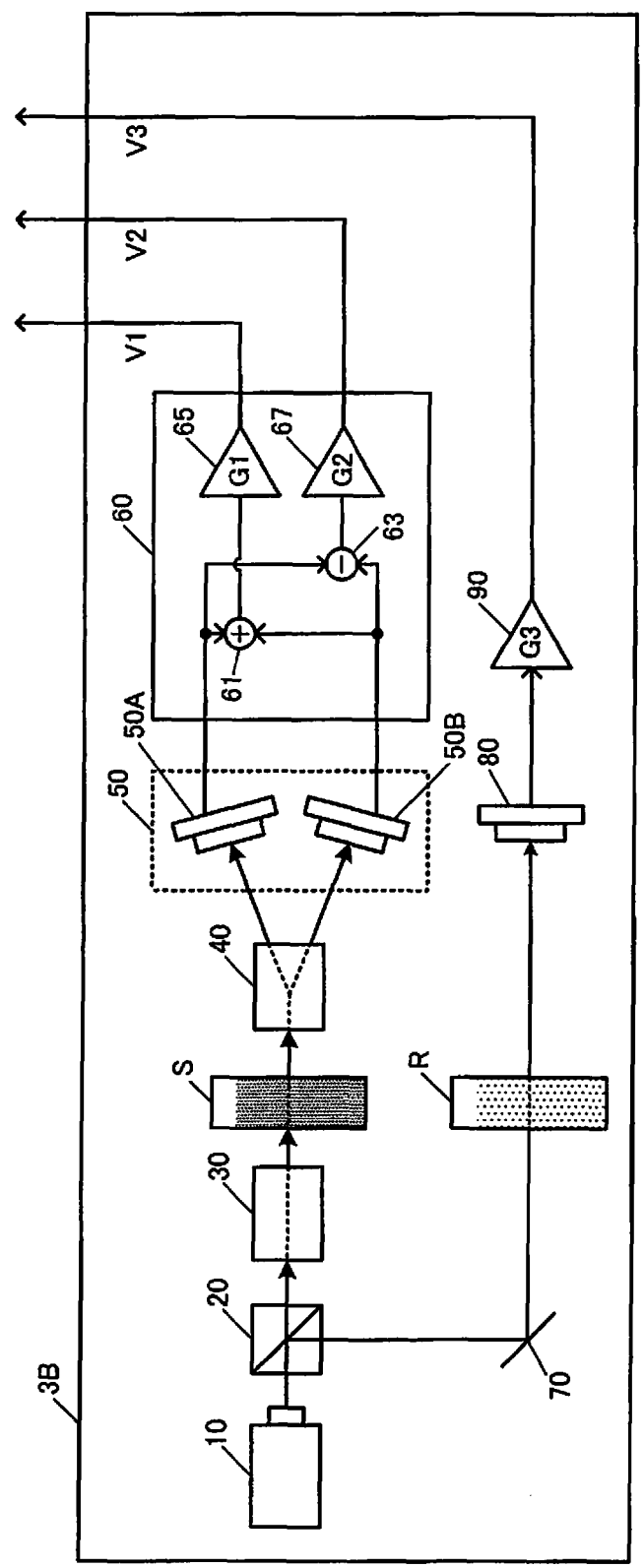
FIG. 6 is an illustration showing a configuration example of the second optical apparatus.

FIG. 6 is an illustration showing an example of a configuration of a second optical apparatus 3B in the second embodiment. In the second optical apparatus 3B in the second embodiment, a reference subject R is placed between a mirror 70 and a second light receiving part 80. In this case, the second light receiving part 80 functions as a reference light receiving part that receives a part of the irradiated light, which is irradiated from the light source to the subject S, through the reference subject.

In the present embodiment, the reference subject is water. The water is placed as the reference subject in order to calculate an absorbance in a protein absorption priority wavelength that cancelled an absorbance related to the water in the subject S. The water is placed as the reference subject R so that the transmitted light that received the absorption by the water is received in the second light receiving part 80. In this case, when an absorbance is calculated in accordance with Equation (12) by using an output voltage "V3" from the second amplifier 90, the absorbance of the water is subtracted from the absorbance of the subject S so that an absorbance in the protein absorption priority wavelength that cancelled the absorption related to the water is obtained. This measurement method is called as "differential measuring method".

However, water tends to change an absorbance depending on a temperature alternation. Therefore, it is necessary to place the subject S and the reference subject R in the environment such that the difference of the temperature is approximately zero. For example, it is appropriate that the constituent parts of the second optical apparatus 3B other than the light source 10 are placed in a thermostatic chamber, or the temperatures of the subject S and the reference subject S are set and stabilized in the same temperature by using a temperature controlling sensor holder.

In this configuration, the effect of the absorption of water does not need to be considered so that the wavelengths in the wavelength regions that are different from the wavelength regions described as an example in the first embodiment can be used for the measurement of the glucose concentration. That is, in the second embodiment, the effect of the absorption of water does not need to be considered so that the measuring light in the wavelengths of the vicinity of infrared light where there are many peaks of the absorption of water can be also used for the measurement of the concentration.

By the way, the principle or the procedure to calculate for a glucose concentration is in the same manner as the first embodiment, and there is no difference except the placement of water as the reference subject R so that the repeated explanation is omitted.

3. Modifications

The embodiments to which the present invention may be applied are not limited to the above described embodiments, and it will be apparent that various modifications can be made in a scope not substantially deviating from the subject matter of the present invention. The modifications will be described below.

3-1. Application Embodiment

The concentration measurement device described in the above embodiment may be incorporated in a measurement system such as a sugar content measurement device that measures the sugar content in fruit, or a blood sugar measurement device that measures the blood sugar level of human.

When it is applied to the sugar content measurement device, for example, the juice of a fruit as the subject S, the sugar content in fruit can be measured in the procedure described in the above embodiments. Also, when it is applied to the blood sugar measurement device, the part having permeability such as earlobe or fingertip of human, a surface skin part of finger, and the like as the part for measurement, the measuring light can be irradiated to the part for measurement. In this case, the organism becomes as the subject S.

3-2. Component of Subject

In the above embodiments, it described that the first component was glucose and the second component was protein, but they were just an example for the description. If a component includes an optical rotation power and an absorbent, any component may be the first component and the second component, and it is possible to measure a concentration of the first component in the same procedures as the above described embodiments.

3-3. Multivariate Analysis

In the above described embodiments, as the multivariate analysis, the simultaneous equations related to an absorption and an optical rotation are used as an example of the analysis method, but the multivariate analysis is not limited to this method. The multivariate analysis such as the principal component analysis or the Partial Least Squares (PLS) method may be applied after the fashion of the principle of the above described embodiments, and it is possible to measure a concentration of a selected component in a subject.

3-4. Selection of Wavelength of Measuring Light

In the above described embodiments, it described that the wavelength region of the measuring light used for the measurement of the glucose concentration was 400 nm to the vicinity of 1300 nm, but it is possible to select a wavelength of the measuring light other than the above wavelength region. For example, according to the absorption histogram of FIG. 4A, it shows that the quantitation error of the glucose concentration in the wavelength region in the vicinity of 1440 nm or the vicinity of 1786 nm is also small. Thus, these wavelength regions may be defined as the absorbance error reducing wavelength region, and a measuring light wavelength for absorbance may be selected in the above wavelength regions.

3-5. Spectral Analysis by Wavelength Sweeping

In the above described embodiments, it was simulated in the case where the wavelength of the light source was irradiated discretely, and it described that the measuring light in which the wavelength was preliminary selected was generated by the light source 10 and irradiated to the subject S. However, when the light source enables to change a wavelength continuously, all of the spectral data of an optical rotation and absorption are stored in the memory part 600 by performing the wavelength sweeping (wavelength sweep). Among them, necessary wavelength data is read and it is used for the concentration calculation.

Figure 7:
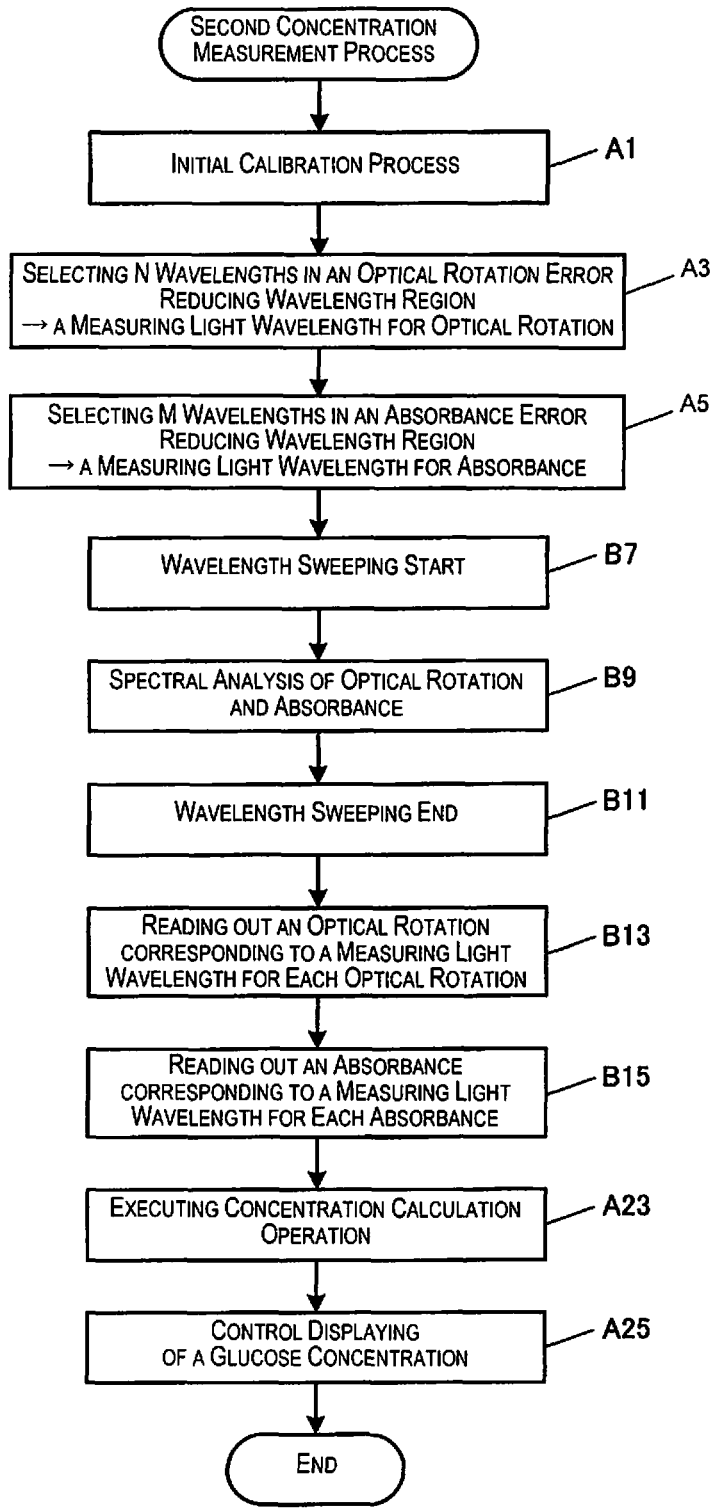
FIG. 7 is a flowchart showing a flow of the second concentration measuring process.

In this case, FIG. 7 is a flowchart showing a flow of the second concentration measurement process that the control part 100 of the above described embodiments executes in addition to the concentration measurement process of FIG. 5. By the way, the same reference symbols are given for the same steps of the concentration measurement process, and the description is omitted.

The control part 100 starts the wavelength sweeping of the light source 10 after the Step A5 (Step B7). Specifically, a wavelength of the measuring light is continuously changed in the predetermined wavelength range (e.g., 400 nm to 2000 nm). The control part 100 performs the spectral analysis of an optical rotation and an absorbance by performing the wavelength sweeping (Step B9). By this spectral analysis, the continuous spectral analysis waveform data for the respective optical rotation and absorbance is obtained. After that, the control part 100 completes the wavelength sweeping (Step B11).

Next, the control part 100 reads out an optical rotation corresponding to each measuring light wavelength for optical rotation selected in Step A3 (Step B13). Also, the control part 100 reads out an absorbance corresponding to each measuring light wavelength for absorbance selected in Step 3A from the absorbance spectral data obtained in the spectral analysis (Step B15). The later processes are the same processes as the concentration measurement process.

3-6. Calculations of Optical Rotation and Absorbance

In the above embodiments, the optical rotation and the absorbance were calculated by using an instantaneous value of an output voltage outputted from the amplifier 60 and the second amplifier 90. However, in addition to this, the optical rotation and the absorbance may be calculated by using an average value of a prescribed time of output voltages. Also, a prescribed time or a prescribed number of the optical rotation and the absorbance is calculated by repeating the steps to calculate the optical rotation and the absorbance by using the instantaneous value of the output voltage, and the optical rotation and the absorbance may be calculated by performing an average processing of these values.

3-7. Optical Device for Polarized Light

In the above described embodiments, the polarization part 30 was configured by, for example, Glan-Thompson prism, but needless to say, it may be configured by other optical devices for polarized light. For example, it may be configured by Glan-Taylor prism that is the same Gran type optical device for polarized light.

Further, in the above described embodiments, it described that the orthogonal separation part 40 was configured by, for example, Wollaston prism, but the optical device for polarized light that configures the orthogonal separation part 40 is also arbitrarily changed. For example, an optical device for polarized light that has an orthogonal separation function such as Glan laser prism or Rochon prism may be configured.

This application claims the benefit of Japanese Patent Application No. 2012-174097, which is filed on Aug. 6, 2012 and hereby incorporated by reference in its entirety.

What is claimed is:
1. A concentration measuring device measuring a concentration of a first constituent of an object to be examined, the concentration measuring device comprising:
 a light source irradiating light toward the object to be examined which includes water, the first constituent having optical rotation and absorbency, and a second constituent having optical rotation and absorbency, such that the light transmits through the object to be examined;

a light detector receiving transmitted light transmitted through the object to be examined and outputting output signals;

a memory storing first measurement data and second measurement data, the first measurement data including at least a first optical rotation coefficient that is predetermined corresponding to a first wavelength and a first absorbance coefficient that is predetermined corresponding to a second wavelength different from the first wavelength, the first optical rotation coefficient and the first absorbance coefficient being related to a first aqueous solution containing water and the first constituent, the second measurement data including at least a second optical rotation coefficient that is predetermined corresponding to the first wavelength and a second absorbance coefficient that is predetermined corresponding to the second wavelength, the second optical rotation coefficient and the second absorbance coefficient being related to a second aqueous solution containing water and the second constituent; and a processor controlling the light source and calculating the concentration of the first constituent, the processor selecting the first wavelength and the second wavelength from a wavelength region in which an absorbance coefficient of water is substantially zero, controlling the light source to irradiate a first measuring light with the first wavelength to the object to be examined, controlling the light source to irradiate a second measuring light with the second wavelength to the object to be examined, calculating an optical rotation value of the first measuring light, which has passed through the object to be examined, based on a first signal of the output signals from the light detector, calculating an absorbance value of the second measuring light, which has passed through the object to be examined, based on a second signal of the output signals from the light detector, obtaining, from the memory, at least the first optical rotation coefficient, the second optical rotation coefficient, the first absorbance coefficient, and the second absorbance coefficient, and calculating the concentration of the first constituent based on at least first and second liner combinations each of which is a linear combination of the concentration of the first constituent and a concentration of the second constituent, the first liner combination including only at least one product of the first optical rotation coefficient and the concentration of the first constituent and at least one product of the second optical rotation coefficient and the concentration of the second constituent, the second liner combination including only at least one product of the first absorbance coefficient and the concentration of the first constituent and at least one product of the second absorbance coefficient and the concentration of the second constituent.

2. The concentration measuring device according to claim 1, wherein the processor selects the first and second wavelengths from the wavelength region which is 400 nm to substantially 1300 nm to control the light source to irradiate the first and second measuring lights to the object to be examined which includes glucose as the first constituent and protein as the second constituent.

3. The concentration measuring device according to claim 2, wherein the processor selects the first wavelength from the wavelength region of 400 nm to 800 nm to control the light source to irradiate the first measuring light for optical rotation.

4. The concentration measuring device according to claim 3, wherein the processor selects the second wavelength from any of the wavelength region of 400 nm to 900 nm, substantially 1100 nm, substantially 1190 nm, and substantially 1300 nm to control the light source to irradiate the second measuring light for absorbance.

5. The concentration measuring device according to claim 4, wherein the processor further selects a third wavelength that is different from the first and second wavelengths from the wavelength region, controls the light source to irradiate to the object to be examined a third measuring light with the third wavelength, obtains, from the memory that further stores, as the first measurement data, at least one of a third optical rotation coefficient and a third absorbance coefficient, which is predetermined corresponding to the third wavelength, and, as the second measurement data, one of a fourth optical rotation coefficient and a fourth absorbance coefficient, which is predetermined corresponding to the third wavelength, the one of the third optical rotation coefficient and the third absorbance coefficient being related to the first aqueous solution, the one of the fourth optical rotation coefficient and the fourth absorbance coefficient being related to the second aqueous solution, calculates one of an optical rotation value and an absorbance value of the third measuring light, which has passed through the object to be examined, based on a third signal of the output signals from the light detector, and calculates the concentration of the first constituent and the second constituent by performing a predetermined multivariate analysis based on at least the first linear combination, the second liner combination, and a third linear combination of the concentration of the first constituent and the concentration of the second constituent, and the third linear combination includes only at least one product of the one of the third optical rotation coefficient and the third absorbance coefficient and the concentration of the first constituent, and at least one product of the one of the fourth optical rotation coefficient and the fourth absorbance coefficient and the concentration of the second constituent.

6. The concentration measuring device according to claim 5, further comprising a reference light detector receiving a part of the second measuring light, which the light source irradiates toward the object to be examined, through a reference material that has water as a main component, and outputting a reference signal, wherein the processor calculates an absorbance value of the reference material based on the reference signal from the reference light detector, and performs subtraction of the absorbance value of the reference material from the absorbance value of the object to be examined to calculate an absorbance of the object to be examined.

7. The concentration measuring device according to claim 1, wherein
the processor further controls the light source to irradiate to the object to be examined a third measuring light with a third wavelength that is different from the first and second wavelengths from the wavelength region,
obtains, from the memory that further stores, as the first measuring data, at least one of a third optical rotation coefficient and a third absorbance coefficient, which is predetermined corresponding to the third wavelength, and, as the second measurement data, one of a fourth optical rotation coefficient and a fourth absorbance coefficient, which is predetermined corresponding to the third wavelength, the one of the third optical rotation coefficient and the third absorbance coefficient being related to the first aqueous solution, the one of the fourth optical rotation coefficient and the fourth absorbance coefficient being related to the second aqueous solution, and
the processor calculates one of an optical rotation value and an absorbance value of the third measuring light, which has passed through the object to be examined, based on a third signal of the output signals from the light detector.

8. The concentration measuring device according to claim 7, wherein
the processor calculates the concentration of the first constituent based on the first linear combination, the second liner combination, and a third linear combination of the concentration of the first constituent and the concentration of the second constituent, the third linear combination includes only at least one product of the one of the third optical rotation coefficient and the third absorbance coefficient and the concentration of the first constituent, and at least one product of the one of the fourth optical rotation coefficient and the fourth absorbance coefficient and the concentration of the second constituent.

9. The concentration measuring device according to claim 7, wherein the processor obtains from the memory, $a_1, b_1, c_1, d_2, e_2, f_2, d_3, e_3,$ and $f_3$ that the memory stores, and calculates the concentration of the first constituent based on a simultaneous equation, which is expressed by $$\begin{cases} a_1 X + b_1 Y + c_1 Z = \alpha \\ d_2 X + e_2 Y + f_2 Z = \beta \\ d_3 X + e_3 Y + f_3 Z = \gamma \end{cases},$$

wherein X is a concentration of glucose as the first constituent, Y is a concentration of albumin that the second constituent includes, Z is a concentration of globulin that the second constituent includes, $\alpha$ is the optical rotation value of the first measuring light, $\beta$ is the absorbance value of the second measuring light, $\gamma$ is the absorbance value of the third measuring light, $a_1$ is an optical rotation coefficient of the glucose that is predetermined corresponding to the first wavelength, $b_1$ is an optical rotation coefficient of the albumin that is predetermined corresponding to the first wavelength, $c_1$ is an optical rotation coefficient of the globulin that is predetermined corresponding to the first wavelength, $d_2$ is an absorbance coefficient of the glucose that is predetermined corresponding to the second wavelength, $e_2$ is an absorbance coefficient of the albumin that is predetermined corresponding to the second wavelength, $f_2$ is an absorbance coefficient of the globulin that is predetermined corresponding to the second wavelength, $d_3$ is an absorbance coefficient of the glucose that is predetermined corresponding to the third wavelength, $e_3$ is an absorbance coefficient of the albumin that is predetermined corresponding to the third wavelength, and $f_3$ is an absorbance coefficient of the globulin that is predetermined corresponding to the third wavelength.

10. A method for controlling a concentration measuring device and measuring a concentration of a first constituent of an object to be examined, the method comprising:
irradiating light by a light source toward the object to be examined which includes water, the first constituent having optical rotation and absorbency, and a second constituent having optical rotation and absorbency, such that the light transmits through the object to be examined;
receiving transmitted light transmitted through the object to be examined and outputting output signals at a light detector;
storing in a memory first measurement data and second measurement data, the first measurement data including at least a first optical rotation coefficient that is predetermined corresponding to a first wavelength and a first absorbance coefficient that is predetermined corresponding to a second wavelength different from the first wavelength, the first optical rotation coefficient and the first absorbance coefficient being related to a first aqueous solution containing water and the first constituent, the second measurement data including at least a second optical rotation coefficient that is predetermined corresponding to the first wavelength and a second absorbance coefficient that is predetermined corresponding to the second wavelength, the second optical rotation coefficient and the second absorbance coefficient being related to a second aqueous solution containing water and the second constituent;
selecting the first wavelength and the second wavelength from a wavelength region in which an absorbance coefficient of water is substantially zero;
controlling the light source to irradiate a first measuring light with the first wavelength to the object to be examined;
controlling the light source to irradiate a second measuring light with the second wavelength to the object to be examined;
calculating an optical rotation value of the first measuring light, which has passed through the object to be examined, based on a first signal of the output signals from the light detector;
calculating an absorbance value of the second measuring light, which has passed through the object to be examined, based on a second signal of the output signals from the light detector;
obtaining, from the memory, at least the first optical rotation coefficient, the second optical rotation coefficient, the first absorbance coefficient, and the second absorbance coefficient; and
calculating a concentration of the first constituent based on at least first and second liner combinations each of which is a liner combination of the concentration of the first constituent and a concentration of the second constituent, the first liner combination including only at least one product of the first optical rotation coefficient and the concentration of the first constituent and at least one product of the second optical rotation coefficient and the concentration of the second constituent, the second liner combination including only at least one product of the first absorbance coefficient and the concentration of the first constituent and at least one product of the second absorbance coefficient and the concentration of the second constituent.

\* \* \* \* \*